US012091541B2

(12) United States Patent
Gigmes et al.

(10) Patent No.: US 12,091,541 B2
(45) Date of Patent: Sep. 17, 2024

(54) SOLID ORGANIC ANTIBACTERIAL MATERIAL

(71) Applicants: Centre National de la Recherche Scientifique, Paris (FR); UNIVERSITÉ D'AIX MARSEILLE, Marseilles (FR); Ecole Centrale de Marseille, Marseilles (FR)

(72) Inventors: Didier Gigmes, Allauch (FR); Yohann Guillaneuf, Allauch (FR); Catherine Guillaneuf, Allauch (FR); Marc René Sauveur Maresca, Vitrolles (FR); Cédric Ysacco, Villeurbanne (FR)

(73) Assignees: Centre national de la recherche scientifique, Paris (FR); UNIVERSITÉ D'AIX MARSEILLE, Marseilles (FR); Ecole Centrale de Marseille, Marseilles (FR)

( * ) Notice: Subject to any disclaimer, the term of this patent is extended or adjusted under 35 U.S.C. 154(b) by 445 days.

(21) Appl. No.: 16/628,851

(22) PCT Filed: Jul. 6, 2018

(86) PCT No.: PCT/EP2018/068449
§ 371 (c)(1),
(2) Date: Jan. 28, 2020

(87) PCT Pub. No.: WO2019/008176
PCT Pub. Date: Jan. 10, 2019

(65) Prior Publication Data
US 2020/0224022 A1 Jul. 16, 2020

(30) Foreign Application Priority Data
Jul. 6, 2017 (FR) ........................................ 1756390

(51) Int. Cl.
*A61L 29/04* (2006.01)
*A61L 29/16* (2006.01)
*C08F 293/00* (2006.01)
*C08L 53/00* (2006.01)

(52) U.S. Cl.
CPC ........... *C08L 53/005* (2013.01); *A61L 29/041* (2013.01); *A61L 29/16* (2013.01); *C08F 293/005* (2013.01); *C08F 2438/02* (2013.01); *C08L 2203/02* (2013.01)

(58) Field of Classification Search
CPC .... C08F 293/00; C08F 293/005; C08L 53/00; C08L 53/005; A61L 29/16; A61L 29/041
See application file for complete search history.

(56) References Cited

U.S. PATENT DOCUMENTS

| 7,745,535 B2* | 6/2010 | Schmidt ............... C08F 293/005 |
| | | 525/89 |
| 2004/0122160 A1* | 6/2004 | Piro ..................... C09D 17/002 |
| | | 523/200 |
| 2005/0147647 A1 | 7/2005 | Glauser et al. |
| 2008/0125513 A1* | 5/2008 | Kristiansen ............. A61L 31/16 |
| | | 523/113 |
| 2011/0207841 A1* | 8/2011 | Kosar ................ B01D 67/0006 |
| | | 521/134 |

FOREIGN PATENT DOCUMENTS

| CN | 102198294 A | 9/2011 |
| EP | 0344692 A2 | 12/1989 |

OTHER PUBLICATIONS

Smets, Wenke et al. Atmospheric Environment vol. 139 pp. 214-221 (Year: 2016).*
Zhang, Xuan et al. Macromolecules vol. 32 pp. 1763-1766 (Year: 1999).*
Yao, Zhikan et al. Desalination vol. 355 pp. 91-98 (Year: 2015).*
Kleijwegt, R.J.T. et al. Chemical Engineering Research and Design vol. 168 pp. 317-326 (Year: 2021).*
Zhikan Yao "Preparation of Tertiary Amine Containing Amphiphilic Copolymer Blended Membrane for Adsorption During Filtration" Chinese Doctoral Dissertations Full-Text Database, Engineering Science and Technology I, Issue 10, 2016, published on Oct. 15, 2016 (8 pages).
Office Action issued in Chinese Application No. 201880058057.3; Dated Jul. 5, 2021 (14 pages).
International Search Report issued in PCT/EP2018/068449 mailed on Oct. 9, 2018 (8 pages).
Written Opinion of the International Searching Authority Issued in PCT/EP2018/068449 mailed on Oct. 9, 2018 (8 pages).
Alvarez-Paino, M. et al.; "Effect of glycounits on the antimicrobial properties and toxicity behavior of polymers based on quaternized DMAEMA"; Biomacromolecules, vol. 16, No. 1, Dec. 10, 2014, pp. 295-303 (9 pages).
Breiner, T. et al.; "Blends of Poly (methacrylate) Block Copolymers with Photoaddressable Segments"; Macromolecules, vol. 40, No. 6, Mar. 1, 2007, pp. 2100-2108 (9 pages).
Wang, Y. et al.; "Antimicrobial and Hemolytic Activities of Copolymers with Cationic and Hydrophobic Groups: A Comparison of Block and Random Copolymers", Macromolecular Bioscience, Aug. 4, 2011, pp. 1499-1504 (6 pages).
Benkhaled, B.T. et al.; "Elaboration of antimicrobial polymeric materials by dispersion of well-defined amphiphilic methacrylic SG1-based copolymers"; Polymer Chemistry, vol. 9, No. 22, Jan. 1, 2018, pp. 3127-3141 (15 pages).

(Continued)

*Primary Examiner* — Marc S Zimmer
*Assistant Examiner* — Jeffrey S Lenihan
(74) *Attorney, Agent, or Firm* — Osha Bergman Watanabe & Burton LLP

(57) ABSTRACT

A solid organic material comprising at least one amphiphilic block copolymer of the methacrylic type, the block copolymer being dispersed in a polymer matrix, the block copolymer having a number-average molar mass (Mn) greater than or equal to 20 000 g/mol; a method for preparing said solid organic material; use of said solid organic material for antibacterial, antimicrobial, antiviral, anti-inflammatory and/or antifungal applications; a medical device comprising said solid organic material.

2 Claims, 4 Drawing Sheets

(56) References Cited

OTHER PUBLICATIONS

S. Utsel et al. "Physical Tuning of Cellulose-Polymer Interactions Utilizing Cationic Block Copolymers Based on PCL and Quaternized PDMAEMA" American Chemical Society, Applied Materials & Interfaces; Nov. 16, 2012 (12 pages).
S. Boisse et al. "PLLA Crystallization in Linear AB and BAB Copolymers of L-Lactide and 2-Dimethylaminoethyl Methacrylate" American Chemical Society, Macromolecules; Sep. 12, 2016 (14 pages).
Office Action issued in Chinese Application No. 201880058057.3; Dated Apr. 21, 2022 (8 pages).

* cited by examiner

SOLID ORGANIC ANTIBACTERIAL MATERIAL

TECHNICAL FIELD

The present disclosure relates to amphiphilic block copolymers of the methacrylic type and solid organic materials; the method of preparation thereof; and the use thereof for antibacterial, antimicrobial, antiviral, anti-inflammatory and/or antifungal application.

BACKGROUND

Microbial resistance to antibiotics has become a public health challenge. Certain antibiotics such as meticillin or vancomycin have in fact become ineffective for combating infections caused by bacteria such as meticillin-resistant or vancomycin-resistant *Staphylococcus aureus* (MRSA or VRSA, respectively). Antibacterial materials may therefore play a role in combating bacterial infections, more particularly in a hospital setting, where infections are notably one of the main causes of complications in intensive care units.

Various methods currently exist for developing antibacterial materials: i) inclusion of biocidal molecules (antibiotics or molecules based on silver, for example) but which are released from the material, leading to a loss of activity of the material, in certain cases side-effects and/or exacerbation of the phenomenon of antimicrobial resistance; ii) surface modification of the material by grafting or coupling, which is a long, expensive, multistep method; iii) use of antibacterial surfactants (at a level of about 10 wt %) for making antimicrobial films.

For some years, antimicrobial peptides (AMPs) have been the subject of many studies attempting to offer an alternative to the existing antibiotics. In contrast to conventional antibiotics, AMPs in fact have the advantage of not inducing resistance, owing to a different mechanism of action mainly affecting the membrane of the bacteria (Michl et al. Polym. Chem. 2014, 19, 5813). However, the main obstacle to the use of AMPs is their cost and their small production volume, the peptides being obtained either by solid-phase peptide synthesis in the case of the synthetic peptides, or being extracted from various natural sources, such as venoms for example. To overcome these problems, various synthetic copolymers have been investigated for mimicking the antimicrobial activity of the AMPs, while being easy to synthesize, and on a large scale. These copolymers, called SMAMPs for "synthetic mimic antimicrobial peptides", are generally amphiphilic copolymers having a hydrophilic moiety, most often charged, which will interact with the membrane of the bacteria and become attached to it, and a hydrophobic moiety which will destabilize or pierce the bacterial membrane (Kuroda et al. Nanomed. Nanobiotechnology 2013, 5, 49; Takahashi et al. Macromol. Biosci. 2013, 13, 1285). Although the mode of action of the SMAMPs reproduces that of the AMPS, their synthesis is in contrast much easier as it is carried out by various polymerization techniques and in particular by radical polymerization, which allows production on a very large scale.

Moreover, Lenoir et al. (Biomacromolecules, 2006, 7, 2291) reported in 2006 the dispersion of poly(ethylene-co-butylene)-b-poly(2-(tert-butylamino)ethyl methacrylate) (PEB-b-PTBAEMA, $M_n$=14000 g/mol) diblock copolymers for conferring antimicrobial properties on films of low-density polyethylene (LDPE). The copolymers were mixed in LDPE at a level of 10 wt % and displayed activity against *E. coli* (Gram −). Zuo et al. (Journal of Applied Polymer Science, 2012, 125, 3537), for their part, reported the development of commercial poly(methyl methacrylate) (PMMA) made antibacterial by mixing with at least 10 wt % of poly(tert-butylamino)ethyl methacrylate) (PTBAEMA, $M_w$≤10000 g/mol), displaying activity against *S. aureus* (Gram +) and *E. coli* (Gram −). Finally, Li et al. (European Polymer Journal, 2014, 51, 120) showed that it was possible to prepare antibacterial polypropylene (PP) by grafting in supercritical $CO_2$ and by reactive extrusion of chains of poly(hexamethylenediamine-guanidinium chloride). This complex method made it possible to develop PP-based materials that are active against bacteria of the *S. aureus* and *E. coli* type.

However, the copolymer used is typically of low molar mass (<15000 g/mol) to imitate the structure of the natural antimicrobial peptides. According to the literature, a higher molar mass would also be accompanied by an increase in hemolytic character of the copolymer (Ganewatta et al. Polymer 2015, 63, A1). Moreover, the amount of copolymer necessary for observing antimicrobial activity is high, around 10 wt %. Furthermore, the activity reported only relates to model bacterial strains (typically *S. aureus* and *E. coli*) that do not include the pathogenic strains, yet these are a crucial health challenge for the future. Finally, the various production methods mentioned above only make it possible to produce organic antibacterial materials of a single given chemical nature (PEHB or PMMA or PP). A versatile method of incorporating the antimicrobial copolymer in organic matrixes of different chemical nature is therefore lacking. As a consequence, there is a need for solid organic materials and a method of preparation thereof making it possible to overcome some of the limitations mentioned above.

SUMMARY

An object of the present disclosure is to supply amphiphilic block copolymers of the methacrylic type and solid organic materials with antibacterial, antimicrobial, antiviral, anti-inflammatory and/or antifungal properties.

According to a first aspect, the aforementioned object, as well as other advantages, are attained by a solid organic material comprising at least one amphiphilic block copolymer of the methacrylic type, the block copolymer being dispersed in a polymer matrix, the block copolymer having a number-average molar mass ($M_n$) greater than or equal to 20 000 g/mol.

According to one or more embodiments, the block copolymer has an $M_n$ less than or equal to 100 000 g/mol. According to one or more embodiments, the block copolymer has a number-average molar mass (Mn) comprised between 20 000 and 70 000 g/mol. According to one or more embodiments, the block copolymer has a number-average molar mass (Mn) comprised between 21 000 and 55 000 g/mol. According to one or more embodiments, the block copolymer has a number-average molar mass (Mn) between 22 000 and 40 000 g/mol.

According to one or more embodiments, the block copolymer is a diblock polymer, i.e., comprising two types of monomers.

According to one or more embodiments, the solid organic material comprises from 0.02 to 10 wt % of the block copolymer. According to one or more embodiments, the solid organic material comprises less than 10 wt % of the block copolymer. According to one or more embodiments, the solid organic material comprises from 0.1 to 4, 6 or 8 wt % of the block copolymer. According to one or more embodiments, the solid organic material comprises from 0.2 to 2 wt % of the block copolymer.

According to one or more embodiments, the block copolymer has at least one hydrophilic moiety, i.e., at least one hydrophilic methacrylic block, and at least one hydrophobic moiety, i.e., at least one hydrophobic methacrylic block.

The term "hydrophilic" is synonymous with (means the same thing as) capable of forming hydrogen bonds, such as with a polar solvent, such as water. The term "hydrophobic" is synonymous with (means the same thing as) not capable of forming hydrogen bonds, such as with a polar solvent, such as water.

According to one or more embodiments, the hydrophilic methacrylic block comprises at least one tertiary amine group and/or quaternary ammonium ion.

According to one or more embodiments, the hydrophilic methacrylic monomer (i.e., hydrophilic repeating unit of the hydrophilic methacrylic block) is selected from the group consisting of an N,N-(dialkylamino)alkyl methacrylate, such as an N,N-(dialkylamino)ethyl methacrylate, and a quaternary ammonium ion of the latter. According to one or more embodiments, at least one of the alkyl functions is a substituted or unsubstituted alkyl and/or comprises between 1 and 8 carbon atoms, such as between 2 and 6 carbon atoms.

The term "unsubstituted" is synonymous with (means the same thing as) not substituted with an atom other than one or more hydrogen atoms.

The term "substituted" is synonymous with (means the same thing as) substituted with at least one element other than a hydrogen atom, for example substituted with at least one hydrocarbon-containing substituent. According to one or more embodiments, the element is selected from the group consisting of an alkyl, an alkenyl, an alkynyl, an aryl, a heteroaryl, an alkylalkenyl, an alkenylalkyl, an alkylalkynyl, an alkynylalkyl, an alkylaryl, an arylalkyl, an alkylheteroaryl, a heteroarylalkyl, an alkenylaryl, an alkenylheteroaryl, an arylalkynyl, a heteroarylalkynyl, an alkynylaryl and an alkynylheteroaryl, the element comprising from 1 to 20 carbon atoms, such as 2 to 18, 3 to 16, 4 to 14 or 5 to 12 carbon atoms; said element optionally comprising one or more heteroatoms, such as for example N, O, S, P, Si, Sn, Ge, As, F, Cl, Br and I; and/or said element optionally comprising one or more functional groups selected from the list consisting of an alkyl, an alkene, an alkyne, an aryl, a heteroaryl, an alcohol, a ketone, a benzoyl, an aldehyde, a carbonate, a carboxylic acid, a carboxylate, an ester, an ether-oxide, a heterocycle, an amine, an amide, an azo, a diazo, a diazoamino, a nitride, a secondary imine, a hydrazine, a hydrazone, an amidine, a carbamate, a guanidine, a carbodiimide, a nitrile, an isonitrile, an imide, an azide, a diimide, a thiol, a thioether, a thioketone, a cyanate, a nitrate, a nitrite, a nitro, a nitroso, an oxime, a pyridyl, a thioether, a disulfide, a sulfinyl, a sulfonyl, a thiocyanate, an isothiocyanate, a thione, a phosphorane, a phosphine, a boronate, a borinate, a silane and a halogen, the functional groups comprising from 0 to 20 carbon atoms, such as 1 to 20, 2 to 18, 3 to 16, 4 to 14 or 5 to 12 carbon atoms.

According to one or more embodiments, the hydrophilic methacrylic monomer is selected from the group consisting of N,N-(dimethylamino)ethyl methacrylate (DMAEMA), N,N-(diethylamino)ethyl methacrylate (DEAEMA) and a quaternary ammonium ion of the latter.

According to one or more embodiments, the hydrophobic methacrylic monomer (i.e., hydrophobic repeating unit of the hydrophobic methacrylic block) is selected from the group consisting of a linear, branched, cyclic or cyclic and branched alkyl methacrylate, having for example from 1 to 20 carbon atoms. According to one or more embodiments, the alkyl methacrylate is selected from the group consisting of methyl methacrylate (MMA) and butyl methacrylate (BMA).

According to one or more embodiments, the hydrophilic methacrylic block and/or the hydrophobic methacrylic block further comprises at least one additional repeating unit such as selected from the group consisting of styrene (S) and acrylonitrile (ACN).

According to one or more embodiments, the block copolymer comprises at least one block selected from PBMA, PMMA, PDMAEMA and PDEAEMA. According to one or more embodiments, the block copolymer comprises at least one of the following formulations: PMMA-b-PDMAEMA, PMMA-b-PDEAEMA, PBMA-b-PDMAEMA, PBMA-b-PDEAEMA, P(MMA-Co-S)-b-PDMAEMA, P(MMA-Co-S)-b-PDEAEMA, P(BMA-Co-S)-b-PDMAEMA, P(BMA-Co-S)-b-PDEAEMA, P(MMA-Co-ACN)-b-PDMAEMA, P(MMA-Co-ACN)-b-PDEAEMA, P(BMA-Co-ACN)-b-PDMAEMA, P(BMA-Co-ACN)-b-PDEAEMA, PMMA-b-P(DMAEMA-Co-S), PMMA-b-P(DEAEMA-Co-S), PBMA-b-P(DMAEMA-Co-S), PBMA-b-P(DEAEMA-Co-S), PMMA-b-P(DMAEMA-Co-ACN), PMMA-b-P(DEAEMA-Co-ACN), PBMA-b-P(DMAEMA-Co-ACN), PBMA-b-P(DEAEMA-Co-ACN), P(MMA-Co-S)-b-P(DMAEMA-Co-S), P(MMA-Co-S)-b-P(DEAEMA-Co-S), P(BMA-Co-S)-b-P(DMAEMA-Co-S), P(BMA-Co-S)-b-P(DEAEMA-Co-S), P(MMA-Co-ACN)-b-P(DMAEMA-Co-ACN), P(MMA-Co-ACN)-b-P(DEAEMA-Co-ACN), P(BMA-Co-ACN)-b-P(DMAEMA-Co-ACN), P(BMA-Co-ACN)-b-P(DEAEMA-Co-ACN), P(MMA-Co-S)-b-P(DMAEMA-Co-ACN), P(MMA-Co-S)-b-P(DEAEMA-Co-ACN), P(BMA-Co-S)-b-P(DMAEMA-Co-ACN), P(BMA-Co-S)-b-P(DEAEMA-Co-ACN), P(MMA-Co-ACN)-b-P(DMAEMA-Co-S), P(MMA-Co-ACN)-b-P(DEAEMA-Co-S), P(BMA-Co-ACN)-b-P(DMAEMA-Co-S) and P(BMA-Co-ACN)-b-P(DEAEMA-Co-S). According to one or more embodiments, the block copolymer comprises one of the following formulations: P(BMA-Co-S)-b-P(DMAEMA-Co-S), and P(BMA-Co-ACN)-b-P(DMAEMA-Co-ACN).

According to one or more embodiments, the block copolymer comprises from 20 to 80 mol % of hydrophilic repeating units. According to one or more embodiments, the block copolymer comprises from 50 to 70 mol % of hydrophilic repeating units.

According to one or more embodiments, the block copolymer comprises from 20 to 80 mol % of hydrophobic repeating units. According to one or more embodiments, the block copolymer comprises from 30 to 50 mol % of hydrophobic repeating units.

According to one or more embodiments, the block copolymer comprises from 3 to 20 wt % of additional repeating units. According to one or more embodiments, the block copolymer comprises from 5 to 10 wt % of additional repeating units.

According to one or more embodiments, the hydrophobic methacrylic block has a number-average molar mass (Mn) comprised between 4000 and 30000 g/mol. According to one or more embodiments, the hydrophobic methacrylic block has a number-average molar mass (Mn) comprised between 6000 and 20000 g/mol.

According to one or more embodiments, the block copolymer has a dispersity (Đ) comprised between 1 and 2.0. According to one or more embodiments, the block copolymer has a dispersity (Đ) comprised between 1.30 and 1.50.

According to one or more embodiments, the hydrophobic methacrylic block has a dispersity (Đ) comprised between 1.20 and 1.50. According to one or more embodiments, the hydrophobic methacrylic block has a dispersity (Đ) comprised between 1.30 and 1.40.

According to one or more embodiments, the polymer matrix comprises at least one repeating unit selected from the group consisting of polyethylene (PE), polypropylene (PP), polycarbonate (PC), polyamide (PA), a polyester, polyurethane (PU), polystyrene (PS), poly(methyl methacrylate) (PMMA), poly(vinyl chloride) (PVC), acrylic resins, the silicones and the thermosetting composites. Examples of polyesters comprise poly(lactic acid) and poly(ethylene terephthalate), etc.

According to one or more embodiments, the polymer matrix comprises at least one repeating unit selected from the group consisting of polystyrene (PS), poly(methyl methacrylate) (PMMA), polycarbonate (PC).

According to a second aspect, the aforementioned objects, as well as other advantages, are attained by a method for preparing a solid organic material, such as the solid organic material according to the first aspect, said method comprising dispersing at least one amphiphilic block copolymer of the methacrylic type in a polymer matrix, wherein the block copolymer has a number-average molar mass ($M_n$) greater than or equal to 20 000 g/mol.

According to one or more embodiments, the method comprises preparing the block copolymer by nitroxide-mediated radical polymerization.

According to one or more embodiments, radical polymerization is carried out in the presence of N-(2-methylpropyl)-N-(1-di ethylphosphono-2,2-dimethylpropyl)-N-oxyl nitroxide, called SG1.

According to one or more embodiments, radical polymerization is carried out in the presence of (N-(2-methylpropyl)-N-(1-diethylphosphono-2,2-dimethylpropyl)-O-(2-carboxylprop-2-yl) alkoxyamine marketed by Arkema under the name BlocBuilder MA.

According to one or more embodiments, preparation of the amphiphilic block copolymer of the methacrylic type comprises: polymerization of one of the hydrophilic or hydrophobic monomers (optionally in the presence of an additional repeating unit) to form a first hydrophilic or hydrophobic block, respectively; then extension of this first block by polymerization of the other hydrophobic or hydrophilic monomer (optionally in the presence of an additional repeating unit) to form the hydrophilic-block-hydrophobic or hydrophobic-block-hydrophilic amphiphilic block copolymer.

According to one or more embodiments, polymerization is carried out by heating the monomers, preferably under inert atmosphere (e.g. under nitrogen or argon), in the presence of a polymerization initiator (BlocBuilder MA or macroalkoxyamine forming the first block of the copolymer) and of free nitroxide SG1.

According to one or more embodiments, polymerization is carried out at a temperature comprised between 80° C. and 130° C. According to one or more embodiments, polymerization is carried out at a temperature of 90° C.

According to one or more embodiments, polymerization is carried out for a time comprised between 4 and 15 h. According to one or more embodiments, polymerization is carried out for a time comprised between 4 and 10 h, such as 5.5 h.

According to one or more embodiments, polymerization is carried out until conversion comprised between 30 and 80% is obtained for each block (hydrophilic and hydrophobic). According to one or more embodiments, polymerization is carried out until conversion comprised between 40 and 60%, such as between 45 and 50%, is obtained for each block (hydrophilic and hydrophobic).

According to one or more embodiments, dispersion of the amphiphilic block copolymer of the methacrylic type in a polymer matrix comprises: preparing a solution comprising a solvent (e.g. THF) and the polymer matrix (e.g. PS or PMMA), adding the block copolymer (quaternized or not) to the solution, and solvent evaporation to obtain the solid organic material.

According to one or more embodiments, the block copolymer comprises at least one hydrophilic methacrylic block comprising at least one tertiary amine group, said method comprising quaternization of the tertiary amine. According to one or more embodiments, quaternization is carried out by means of methyl iodide (MeI). According to one or more embodiments, the percentage quaternization of the tertiary amine is from 2.0 mol % (relative to the polymer chains) to 100%.

According to a third aspect, the aforementioned objects, as well as other advantages, are attained by a use of a solid organic material as claimed in any one of the embodiments of the first aspect for nontherapeutic applications, be they antibacterial and/or antimicrobial and/or antiviral and/or anti-inflammatory and/or antifungal.

According to a fourth aspect, the aforementioned objects, as well as other advantages, are attained by a device comprising a solid organic material as claimed in any one of the embodiments of the first aspect.

According to one or more embodiments, the device is selected from the group consisting of a catheter.

According to an additional aspect, the aforementioned objects, as well as other advantages, are attained by an amphiphilic block copolymer of the methacrylic type having a number-average molar mass (Mn) greater than or equal to 20 000 g/mol, for example for antibacterial and/or antimicrobial and/or antiviral and/or anti-inflammatory and/or antifungal application. According to one or more embodiments, the amphiphilic block copolymer of the methacrylic type comprises the features as defined above forming part of the solid organic material. It is also envisaged that the amphiphilic block copolymer of the methacrylic type may be used as a medicament.

According to an additional aspect, the aforementioned objects, as well as other advantages, are attained by an organic material according to any one of the embodiments of the first aspect for use thereof as a medicament, for example as an antibacterial and/or antiviral and/or antifungal and/or anti-inflammatory medicament.

Embodiments according to the aspects referred to above as well as additional advantages will become clearer on reading the description illustrated by the following figures and the accompanying claims.

DETAILED DESCRIPTION

Figure 1:
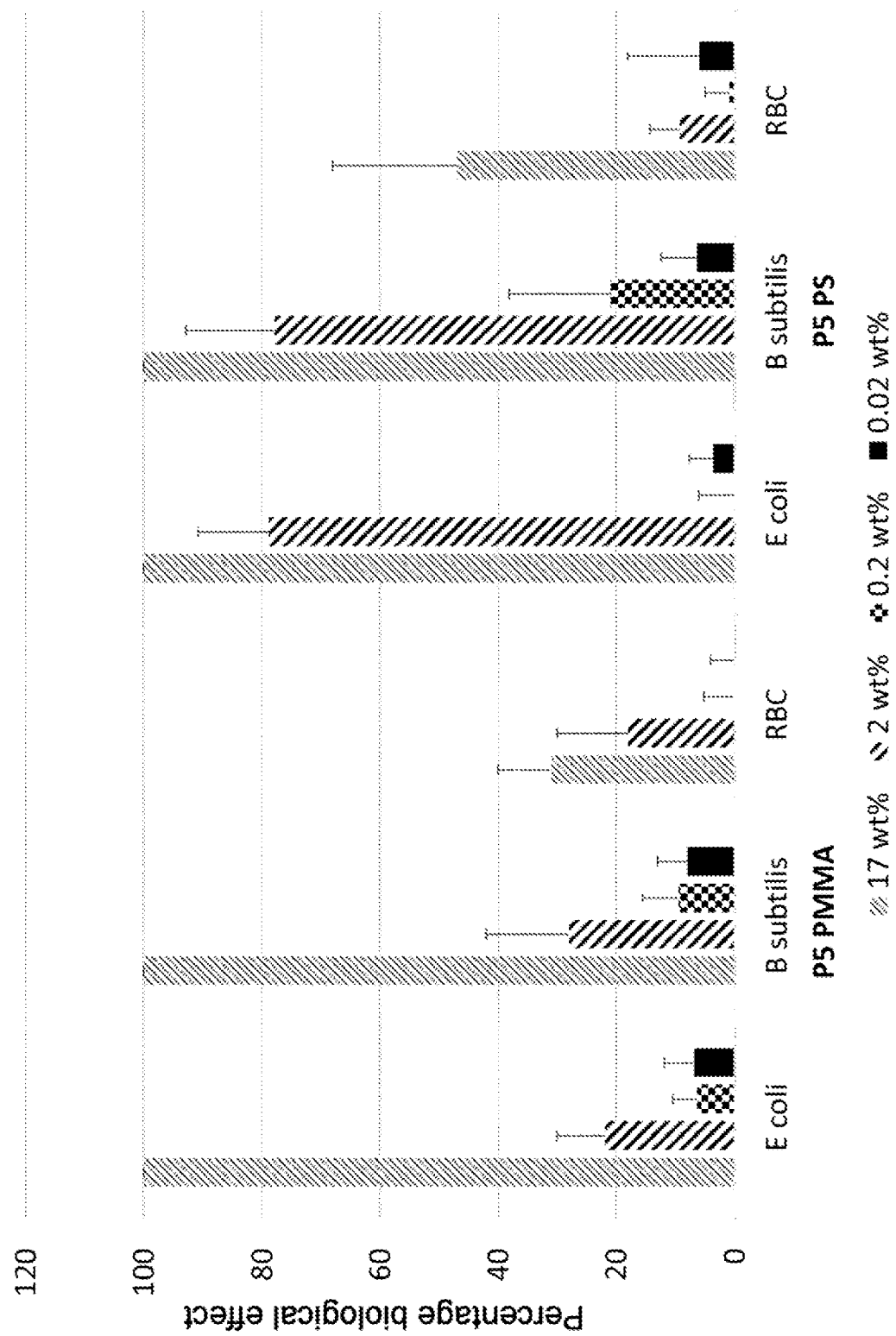
FIGS. 1 to 4 show diagrams illustrating the antibacterial activity and the hemolytic character of solid materials according to embodiments of the present disclosure.

In the following detailed description of embodiments of the present disclosure, numerous specific details are disclosed in order to provide a deeper understanding of the present disclosure. However, it will be apparent to a person skilled in the art that the present disclosure can be implemented without these specific details. In other cases, features that are well known have not been described in detail, to avoid making the description needlessly complicated.

Hereinafter, the term "comprise" is synonymous with (means the same thing as) "include", "contain", and is inclusive or open and does not exclude other elements that are not described or shown. Furthermore, in the present disclosure, the terms "about" and "roughly" are synonymous with (mean the same thing as) a lower and/or upper margin of 10% of the respective value.

The present disclosure relates to a solid organic material. The solid organic material comprises at least one amphiphilic block copolymer of the methacrylic type, the block copolymer being dispersed in a polymer matrix, the block copolymer having a number-average molar mass (Mn) greater than or equal to 20 000 g/mol.

According to one or more embodiments, the solid organic material possesses antibacterial, antimicrobial, antiviral, anti-inflammatory and/or antifungal properties.

According to one or more embodiments, improved dispersion of the block copolymer in the polymer matrix is obtained, without, however, increasing the toxicity of the solid organic material or decreasing the antibacterial, antimicrobial, antiviral, anti-inflammatory and/or antifungal activity.

According to one or more embodiments, the solid organic materials are notably active against bacteria of the Gram + and Gram − and pathogens.

According to one or more embodiments, the solid organic materials do not lose their activity over time and do not have to be replaced in the case of prolonged use or deterioration.

According to one or more embodiments, the solid organic materials do not release biocidal compounds into the environment.

According to one or more embodiments, the solid organic material is suitable for preventing release of molecules and therefore loss of activity over time, problems of side-effects and contamination of the patient and/or the environment.

According to one or more embodiments, the solid organic material is entirely antibacterial, and not only in the surface of the material, which is an important plus in the case of degradation of said material.

The present disclosure also relates to a method for preparing a solid organic material, such as the solid organic material according to the first aspect, said method comprising dispersing at least one amphiphilic block copolymer of the methacrylic type in a polymer matrix, wherein the block copolymer has a number-average molar mass (Mn) greater than or equal to 20 000 g/mol.

According to one or more embodiments, the method according to the second aspect is a method that is simple, versatile, suitable for a wide range of polymer matrixes (e.g. PS, PMMA, PVC, silicones and thermosetting composites) and it can be implemented to large scale, making it possible to confer permanent antibacterial and antimicrobial properties to conventional polymer matrixes against various strains of bacteria (Gram + (B. subtilis) and Gram − (E. coli)). Moreover, these solid organic materials may be of interest as antifungal, antiviral and anti-inflammatory materials.

According to one or more embodiments, the method makes it possible to develop solid organic materials according to the first aspect by simple dispersion, in conventional polymer matrixes (e.g. PS, PVC, PMMA), of amounts, preferably small (e.g. <10 wt %), of amphiphilic block copolymers of the methacrylic type, the copolymer being usable as an additive at a low percentage by weight.

According to one or more embodiments, the amphiphilic block copolymers of the methacrylic type are capable of self-organizing in various matrixes, ensuring that they are dispersed uniformly in the solid organic material.

According to one or more embodiments, the method of preparation also has the advantage of avoiding release of molecules and therefore loss of activity over time, problems of side-effects and contamination of the patient and/or the environment.

According to one or more embodiments, the method of preparation ensures that the whole material is antibacterial, an important plus in the case of degradation of the material.

The present disclosure also relates to devices comprising a solid organic material according to the first aspect. In fact, the solid organic materials according to the present disclosure are suitable for developing antibacterial and/or antimicrobial devices, such as (venous) catheters, no longer requiring regular replacement (roughly every 3 weeks) in the case of prolonged use. These devices may also offer advantages as antifungal, antiviral and anti-inflammatory materials.

The present disclosure also relates to the amphiphilic block copolymers of the methacrylic type considered alone. Specifically, the present disclosure relates to an amphiphilic block copolymer of the methacrylic type having a number-average molar mass (Mn) greater than or equal to 20 000 g/mol, for example for antiviral, anti-inflammatory and/or antifungal application.

Examples of amphiphilic block copolymers of the methacrylic type, of solid organic materials and of methods of preparation according to the aforementioned aspects are described below.

Synthesis and Characterization of PBMA-b-PDMAEMA Amphiphilic Diblock Copolymers

A series of PBMA-b-PDMAEMA amphiphilic diblock copolymers were prepared by nitroxide-mediated radical polymerization (NMP) by using the BlocBuilder MA alkoxyamine as initiator and by adding a comonomer for controlling the molar masses and the molar mass distribution. In these examples, 10 mol % of styrene (S) or of acrylonitrile (ACN) was used. The diblock copolymers have the following structure:

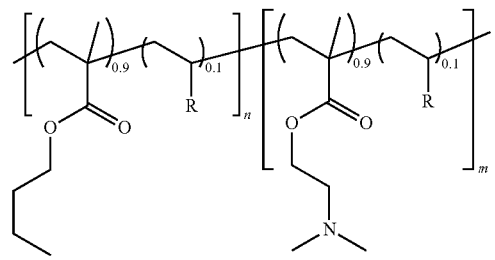

wherein n and m are the degree of polymerization of each block, and R is a styrene or an acrylonitrile. In these examples, the percentage of the hydrophobic group and the molar mass of the amphiphilic diblock copolymer were varied.

The synthesis of (PBMA$_{7000}$-b-PDMAEMA$_{45800}$) (P8) is presented here as an example of a method of preparation according to the second aspect. This synthesis is applicable to all the block copolymers according to the present disclosure. BMA (hydrophobic monomer, 50 g, 0.35 mol), styrene (3.66 g, 0.035 mol), BlocBuilder MA (1.27 g, 3.33 mmol) and SG1 (N-(2-methylpropyl)-N-(1-diethylphosphono-2,2-dimethylpropyl)-N-oxyl) nitroxide, 100 mg, 0.33 mmol) are heated to 90° C. under a nitrogen atmosphere. Samples are taken periodically to monitor the conversion and the molar mass. The reaction is stopped when the conversion reaches 45% (e.g. 2 hours). The conversion is determined by $^1$H NMR (Bruker spectrometer, 300 MHz, CDCl$_3$) by comparing the peaks of the —CH$_2$— groups near the ester function of the monomer (δ=4.11 ppm) and of the polymer (δ=3.91 ppm). The PBMA is then recovered by precipitation in a cold mixture of MeOH/H$_2$O (4/1 by volume) and analyzed by SEC/DMF (size exclusion chromatography PL120 (Polymer Laboratories, England) with DMF as eluent) to obtain the values of number-average molar mass (Mn) and dispersity (Đ; Mw/Mn) (Mn=7000 g·mol$^{-1}$, Đ=1.41). After drying for 24 h under vacuum, PBMA is used for initiating polymerization of the hydrophilic monomer (DMAEMA) to obtain the corresponding PBMA-b-PDMAEMA diblock copolymer. For this purpose, PBMA (1 g), styrene (662 mg, 6.36 mmol), DMAEMA (10 g, 63.6 mmol), 1,4-dioxane (5 ml) and SG1 (4 mg, 0.0125 mmol) are heated to 90° C. under a nitrogen atmosphere. Samples are taken periodically for monitoring the conversion by $^1$H NMR (Bruker spectrometer, CDCl$_3$, 400 MHz) and the value of Mn is determined by SEC/DMF. The reaction is stopped when the conversion is close to 50%. The final PBMA-b-PDMAEMA diblock copolymer is then isolated by precipitation in cold pentane. The copolymer obtained P8 is analyzed by $^1$H NMR and SEC/DMF, obtaining a composition having $F_{DMAEMA}$=0.60 (molar ratio of DMAEMA in the final copolymer), Mn=45800 g·mol$^{-1}$ and Đ=1.37.

Synthesis and Characterization of Amphiphilic PMMA-b-PDMAEMA Diblock Copolymers

A series of amphiphilic PMMA-b-PDMAEMA diblock copolymers were prepared by nitroxide-mediated radical polymerization (NMP) by using the BlocBuilder MA alkoxyamine as initiator and by adding a comonomer for controlling the molar masses and the molar mass distribution. In these examples, 10 mol % of styrene (S) or of acrylonitrile (ACN) was used. The diblock copolymers have the following structure:

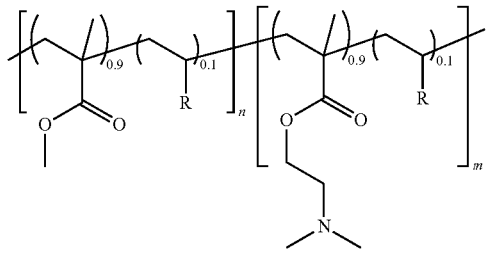

wherein n and m are the degree of polymerization of each block, and R is a styrene or an acrylonitrile.

The synthesis of (PMMA$_{9300}$-b-PDMAEMA$_{40000}$) (P1) is presented here as an example of a method of preparation according to the second aspect. This synthesis is applicable to all the block copolymers according to the present disclosure. MMA (methyl methacrylate, 50 g, 0.50 mol), styrene (5.2 g, 0.05 mol), BlocBuilder MA (954 mg, 2.5 mmol) and SG1 (74 mg, 0.25 mmol) are heated to 90° C. under a nitrogen atmosphere. Samples are taken periodically to monitor the conversion and the molar mass. The reaction is stopped when the conversion reaches 45% (e.g. 2 hours). The conversion is determined by $^1$H NMR (Bruker spectrometer, 300 MHz, CDCl$_3$) by comparing the peaks of the —CH$_3$— groups near the ester function of the monomer (δ=4.11 ppm) and of the polymer (δ=3.91 ppm). The PMMA is then recovered by precipitation in a cold mixture of MeOH/H$_2$O (4/1 by volume) and analyzed by SEC/DMF to obtain the values of number-average molar mass (Mn) and of dispersity (Đ) (Mn=9300 g·mol$^{-1}$, Đ=1.30). After drying for 24 h under vacuum, PMMA is used for initiating polymerization of the DMAEMA and to obtain the corresponding PMMA-b-PDMAEMA diblock copolymer. For this purpose, PMMA (1 g), styrene (662 mg, 6.37 mmol), DMAEMA (10 g, 63.6 mmol), 1,4-dioxane (5 ml) and SG1 (4 mg, 0.0125 mmol) are heated to 90° C. under a nitrogen atmosphere. Samples are taken periodically for monitoring the conversion by $^1$H NMR (Bruker spectrometer, CDCl$_3$, 400 MHz) and the value of Mn is determined by SEC/DMF. The reaction is stopped when the conversion is close to 50%. The final PMMA-b-PDMAEMA diblock copolymer is then isolated by precipitation in cold pentane. The copolymer obtained P1 is analyzed by $^1$H NMR and SEC/DMF, obtaining a composition having $F_{DMAEMA}$=0.74, Mn=40000 g·mol$^{-1}$ and Đ=1.46.

Synthesis and Characterization of Amphiphilic PMMA-b-PDEAEMA Diblock Copolymers

A series of amphiphilic PMMA-b-PDEAEMA diblock copolymers were prepared by nitroxide-mediated radical polymerization (NMP) by using the BlocBuilder MA alkoxyamine as initiator and by adding a comonomer for controlling the molar masses and the molar mass distribution. In these examples, 10 mol % of styrene (S) or of acrylonitrile (ACN) was used. The diblock copolymers have the following structure:

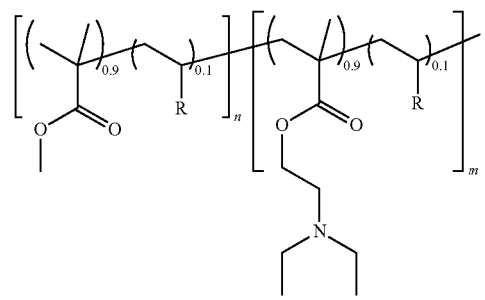

wherein n and m are the degree of polymerization of each block, and R is a styrene or an acrylonitrile.

The synthesis of (PMMA$_{9300}$-b-PDEAEMA$_{25500}$) (P2) is presented here as an example of a method of preparation according to the second aspect. This synthesis is applicable to all the block copolymers according to the present disclosure. MMA (methyl methacrylate, 50 g, 0.50 mol), styrene (5.2 g, 0.05 mol), BlocBuilder MA (954 mg, 2.5 mmol) and SG1 (74 mg, 0.25 mmol) are heated to 90° C. under a nitrogen atmosphere. Samples are taken periodically to monitor the conversion and the molar mass. The reaction is stopped when the conversion reaches 45% (e.g. 2 hours). The conversion is determined by $^1$H NMR (Bruker spectrometer, 300 MHz, CDCl$_3$) by comparing the peaks of the —CH$_3$— groups near the ester function of the monomer (δ=4.11 ppm) and of the polymer (δ=3.91 ppm). The PMMA is then recovered by precipitation in a cold mixture of MeOH/H$_2$O (4/1 by volume) and analyzed by SEC/DMF to obtain the values of number-average molar mass (Mn) and of dispersity (Đ) (Mn=9300 g·mol$^{-1}$, Đ=1.30). After drying for 24 h under vacuum, PMMA is used for initiating polymerization of the hydrophilic monomer of 2-(diethylamino)ethyl methacrylate (DEAEMA) and obtain the corresponding PMMA-b-PDEAEMA diblock copolymer. For this purpose, PMMA (1.3 g), styrene (562 mg, 5.4 mmol), DEAEMA (10 g, 54 mmol), 1,4-dioxane (5 ml) and SG1 (3 mg, 0.01 mmol) are heated to 90° C. under a nitrogen atmosphere. Samples are taken periodically for monitoring the conversion by $^1$H NMR (Bruker spectrometer, CDCl$_3$, 400 MHz) and the value of Mn is determined by SEC/DMF. The reaction is stopped when the conversion is close to 50%. The final PMMA-b-PDEAEMA diblock copolymer is then isolated by precipitation in cold pentane. The copolymer obtained P2 is analyzed by $^1$H NMR and SEC/DMF, obtaining a composition having $F_{DMAEMA}$=0.58, Mn=25500 g·mol$^{-1}$ and Đ=1.30.

Synthesis and Characterization of Amphiphilic PBMA-b-PDEAEMA Diblock Copolymers

A series of amphiphilic PBMA-b-PDEAEMA diblock copolymers were prepared by nitroxide-mediated radical polymerization (NMP) by using the BlocBuilder MA alkoxyamine as initiator and by adding a comonomer for controlling the molar masses and the molar mass distribution. In these examples, 10 mol % of styrene (S) or of acrylonitrile (ACN) was used. The diblock copolymers have the following structure:

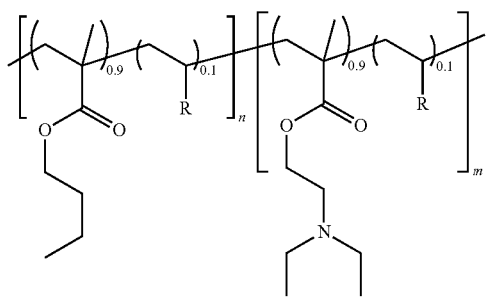

in which n and m denote the degree of polymerization of each block, and R is a styrene or an acrylonitrile. In these examples, the percentage of hydrophobic group and the molar mass of the amphiphilic diblock copolymer were varied.

The synthesis of (PBMA$_{9300}$-b-PDEAEMA$_{18000}$) (P4) is presented here as an example of a method of preparation according to the second aspect. This synthesis is applicable to all the block copolymers according to the present disclosure. BMA (hydrophobic monomer, 50 g, 0.35 mol), styrene (3.66 g, 0.035 mol), BlocBuilder MA (952 g, 2.49 mmol) and SG1 (73 mg, 0.25 mmol) are heated to 90° C. under a nitrogen atmosphere. Samples are taken periodically to monitor the conversion and the molar mass. The reaction is stopped when the conversion reaches 45% (e.g. 2 hours). The conversion is determined by $^1$H NMR (Bruker spectrometer, 300 MHz, CDCl$_3$) by comparing the peaks of the —CH$_2$— groups near the ester function of the monomer ($\delta$=4.11 ppm) and of the polymer ($\delta$=3.91 ppm). The PBMA is then recovered by precipitation in a cold mixture of MeOH/H$_2$O (4/1 by volume) and analyzed by SEC/DMF to obtain the values of number-average molar mass (Mn) and dispersity (Đ; Mw/Mn) (Mn=9300 g·mol$^{-1}$, Đ=1.24). After drying for 24 h under vacuum, PBMA is used for initiating polymerization of the hydrophilic monomer (DMAEMA) and to obtain the corresponding PBMA-b-PDEAEMA diblock copolymer. For this purpose, PBMA (1.5 g), styrene (562 mg, 5.4 mmol), DEAEMA (10 g, 54 mmol), 1,4-dioxane (5 ml) and SG1 (4 mg, 0.0125 mmol) are heated to 90° C. under a nitrogen atmosphere. Samples are taken periodically for monitoring the conversion by $^1$H NMR (Bruker spectrometer, CDCl$_3$, 400 MHz) and the value of Mn is determined by SEC/DMF. The reaction is stopped when the conversion is close to 50%. The final PBMA-b-PDEAEMA diblock copolymer is then isolated by precipitation in cold pentane. The copolymer obtained P4 is analyzed by $^1$H NMR and SEC/DMF, obtaining a composition having $F_{DMAEMA}$=0.31, Mn=18000 g·mol$^{-1}$ and Đ=1.52.

Quaternization of the Block Copolymers

Quaternization of the examples of diblock copolymers was carried out by modifying the amine function of DMAEMA or of DEAEMA with methyl iodide (MeI). Different quaternization yields were targeted, such as 0% (i.e. no quaternization), 2%, and 100% (i.e. quaternization of all the amine functions). The diblock copolymer is dissolved in a solvent (e.g. 1 g of copolymer in 10 ml of DMF) and MeI is added to the solution, for example slowly at room temperature. After stirring for 24 h, the quaternized copolymer is dialyzed against ultrapure water (e.g. Milli-Q® water) for 3 days and then lyophilized prior to analysis by $^1$H NMR.

TABLE 1 amphiphilic block copolymer of the methacrylic type P1 to P18 (with 10 mol % of styrene or acrylonitrile per methacrylic monomer)

| # | block copolymer | S or ACN | % of the hydrophilic block | % quat. MeI | Mn (g/mol) | Mn of the hydrophobic block (g/mol) | Đ |
|---|---|---|---|---|---|---|---|
| P1 | PMMA-b-PDMAEMA | S | 74% | 2 mol % | 40000 | 9300 | 1.46 |
| P2 | PMMA-b-PDEAEMA | S | 58% | 2 mol % | 25500 | 9300 | 1.30 |
| P3 | PBMA-b-PDMAEMA | S | 49% | 2 mol % | 35200 | 9300 | 1.28 |
| P4 | PBMA-b-PDEAEMA | S | 31% | 2 mol % | 18000 | 9300 | 1.52 |
| P5 | PBMA-b-PDMAEMA | S | 46% | 2 mol % | 61600 | 20200 | 1.60 |
| P6 | PBMA-b-PDMAEMA | S | 1-9% | 2 mol % | 28700 | 20200 | 1.24 |
| P7 | PBMA-b-PDMAEMA | S | 38% | 2 mol % | 17700 | 7000 | 1.38 |
| P8 | PBMA-b-PDMAEMA | S | 60% | 2 mol % | 45800 | 7000 | 1.37 |
| P9 | PBMA-b-PDMAEMA | S | 40% | 2 mol % | 22900 | 9300 | 1.24 |
| P10 | PBMA-b-PDMAEMA | S | 37% | 2 mol % | 22600 | 9300 | 1.27 |
| P11 | PBMA-b-DMAEMA | S | 42% | 2 mol % | 22100 | 7000 | 1.26 |
| P12 | PBMA-b-PDMAEMA | S | 62% | 2 mol % | 52800 | 7000 | 1.26 |
| P13 | PBMA-b-PDMAEMA | ACN | 35% | 2 mol % | 22400 | 12800 | 1.32 |
| P14 | PBMA-b-PDMAEMA | S | 73% | 0 mol % | 31300 | 6400 | 1.54 |
| P15 | PBMA-b-PDMAEMA | ACN | 64% | 0 mol % | 20500 | 9300 | 1.34 |
| P16 | PBMA-b-PDMAEMA | S | 73% | 100 mol % | 31300 | 6400 | 1.54 |
| P17 | PBMA-b-PDMAEMA | ACN | 64% | 100 mol % | 20500 | 9300 | 1.34 |
| P18 | PBMA-b-PDMAEMA | ACN | 72% | 100 mol % | 20500 | 9000 | 1.45 |

Antimicrobial Activities of the Amphiphilic Block Copolymers of the Methacrylic Type in Solution The antimicrobial activity of the copolymers P1-P18 was tested. Various Gram-negative strains were used: *Escherichia coli* (ATCC 8739), *Pseudomonas aeruginosa* (ATCC CRM-9027) and *P. aeruginosa* FQR (Fluoroquinone-resistant) (CIP 107398). Gram-positive strains were also used: *Staphylococcus aureus* (ATCC CRM-6538P) and meticillin-resistant *S. aureus* (MRSA USA300) (ATCC BAA-1717 USA 300 CA-MRSA). The antimicrobial activity of the block copolymers was evaluated by determining the minimum inhibitory concentration (MIC). The MIC was determined using serial dilutions in pairs of antimicrobial agents in bacterial liquid media as described by the National Committee of Laboratory Clinical Standards (Comité national des normes cliniques de laboratoire, NCCLS) (NCCLS, 1997). Briefly, individual colonies of the various bacterial strains cultured on Luria-Bertani (LB) agar plates are used for inoculating liquid bacterial culture medium (LB or Mueller-Hinton (MH)). The tubes are incubated overnight at 37° C. with stirring (200 rev/min). On the next day, the bacterial suspensions (optical density OD>1.0) are diluted 1/100 in 3 ml of fresh MH or LB medium and incubated at 37° C., 200 rev/min until the bacteria reach the logarithmic growth phase (OD about 0.6). The bacteria are then diluted in MH or LB medium to reach a bacterial density of around $10^{E5}$ bacteria/ml. 135 µl of bacterial suspension is then added to each of the 96 wells of a sterile polypropylene microplate (Greiner BioOne) already containing 15 µl of serially diluted antimicrobial (1:2 in distilled water). The plates are incubated at 37° C. for 18-24 h before measurement of $OD_{600\,nm}$ using a microplate reader. The MIC is defined as the lowest concentration of antimicrobial that inhibits visible growth of the organism (99% inhibition). The results are presented in Tables 2 and 3 (NS=not soluble).

TABLE 2

| | | MIC (µM) in LB medium | | | |
|---|---|---|---|---|---|
| | Block copolymer | *E coli* | *B subtilis* | *S aureus* | *P aeruginosa* |
| P1 | PMMA-b-PDMAEMA | 2.6 | 1.3 | >21 | 2.6 |
| P2 | PMMA-b-PDEAEMA | 9.35 | 9.35 | >37 | 9.35 |
| P3 | PBMA-b-PDMAEMA | 5.75 | 2.88 | >23 | 2.88 |
| P4 | PBMA-b-PDEAEMA | 10 | 5 | >40 | 10.00 |
| P5 | PBMA-b-PDMAEMA | 4.77 | 2.37 | >38 | 5 |
| P6 | PBMA-b-PDMAEMA | NS | NS | NS | NS |
| P7 | PBMA-b-PDMAEMA | 5 | >20 | | |
| P8 | PBMA-b-PDMAEMA | 0.98 | 1 | >15.8 | 1 |
| P9 | PBMA-b-PDMAEMA | 5 | 3 | | |
| P10 | PBMA-b-PDMAEMA | 3 | 1 | | |
| P11 | PBMA-b-DMAEMA | 20 | 20 | | |
| P12 | PBMA-b-PDMAEMA | 1 | 1 | | |
| P13 | PBMA-b-PDMAEMA | 20 | 10 | | |
| P14 | PBMA-b-PDMAEMA | 2.5 | | | |
| P15 | PBMA-b-PDMAEMA | 10 | | | |
| P16 | PBMA-b-PDMAEMA | >20 | | | |
| P17 | PBMA-b-PDMAEMA | 5 | | | |

TABLE 3

| | | MIC (µM) in MH medium | | | | | |
|---|---|---|---|---|---|---|---|
| | Block copolymer | *E coli* | *B subtilis* | *S aureus* | *Pseudomonas* FQR | MRSA | *E faecalis* VER |
| P1 | PMMA-b-PDMAEMA | 5.250 | 0.660 | 21.300 | 2.6 | 2.6 | >21.3 |
| P2 | PMMA-b-PDEAEMA | >37 | >37 | >37 | 9.35 | >37 | >37.4 |
| P3 | PBMA-b-PDMAEMA | 5.750 | 0.360 | 23.100 | 1.4 | 2.8 | >23.1 |
| P4 | PBMA-b-PDEAEMA | >40 | 20.000 | >40 | 10 | 5 | >40.2 |
| P5 | PBMA-b-PDMAEMA | 9.550 | 1.180 | 19.100 | 2.4 | 4.75 | 38.2 |
| P6 | PBMA-b-PDMAEMA | NS | NS | NS | NS | NS | NS |
| P7 | PBMA-b-PDMAEMA | >20 | >20 | | 6.5 | >20 | >26.1 |
| P8 | PBMA-b-PDMAEMA | 1.975 | 0.490 | 7.900 | 0.98 | 0.98 | 15.8 |
| P9 | PBMA-b-PDMAEMA | 1.250 | 0.313 | | 2.5 | 5 | 20 |
| P10 | PBMA-b-PDMAEMA | 1.250 | 0.625 | | 2.5 | 5 | >20 |
| P11 | PBMA-b-DMAEMA | >20 | 0.625 | | 20 | 1.25 | 1.25 |
| P12 | PBMA-b-PDMAEMA | 0.625 | 0.150 | | 2.5 | 1.25 | 20 |
| P13 | PBMA-b-PDMAEMA | 20.000 | 10.000 | | 20 | 1.25 | 2.5 |
| P14 | PBMA-b-PDMAEMA | 0.6 | 0.3 | | 0.3 | 0.6 | |
| P15 | PBMA-b-PDMAEMA | 0.6 | 0.3 | | 2.5 | 1.25 | |
| P16 | PBMA-b-PDMAEMA | 0.6 | 0.6 | | 1.25 | 0.15 | |
| P17 | PBMA-b-PDMAEMA | 0.6 | 0.15 | | 0.6 | 0.07 | |
| P18 | PBMA-b-PDMAEMA | 2.5 | 0.31 | | 5.0 | 0.31 | |

Hemolytic Characters of the Amphiphilic Block Copolymers of the Methacrylic Type in Solution The hemolytic character of the copolymers P1-P17 was tested in solution. Specifically, the hemolytic activity was determined from the loss of hemoglobin from human erythrocytes (obtained from Divbioscience, NL). The human erythrocytes were washed 3 times with a phosphate-buffered saline solution (PBS) and concentrated by centrifugation at 800 g for 5 min. The human erythrocytes were then resuspended in PBS at a final concentration of 8%. 135 µl of human erythrocytes was then added to each of the 96 wells of a sterile microplate containing 15 µl of diluted antimicrobials (1:2 in distilled water). After 1 h at 37° C., the microplate was centrifuged at 800 g for 5 min. 100 µl was then carefully collected and transferred to a new 96-well microplate and the OD was measured at 405 nm. The hemolysis caused by the copolymers was expressed as percentage hemolysis, Triton-X100 at 0.1% (v:v) being used as positive control giving 100% hemolysis. The results are presented in Table 4.

Table 2-4: Antibacterial Activities and Hemolytic Characters of the Diblock Copolymers in Solution (HMC represents the concentration causing 100% hemolysis and HC50 represents the concentration causing 50% hemolysis; hRBC and sRBC denote "human red blood cell" and "sheep red blood cell", respectively).

TABLE 4

| | | HMC (µM) | | HC50 (µM) | |
|---|---|---|---|---|---|
| | Block copolymer | hRBC | sRBC | hRBC | sRBC |
| P1 | PMMA-b-PDMAEMA | 10.6 | >21.3 | 2.6-5.3 | >21.3 |
| P2 | PMMA-b-PDEAEMA | <0.36 | <0.36 | <0.36 | <0.36 |
| P3 | PBMA-b-PDMAEMA | 5.75 | >23.1 | 1.4-2.8 | >23.1 |
| P4 | PBMA-b-PDEAEMA | <0.39 | <0.39 | <0.39 | <0.39 |
| P5 | PBMA-b-PDMAEMA | 5 | >38 | 0.59-1.19 | >38 |
| P6 | PBMA-b-PDMAEMA | NS | NS | NS | NS |
| P7 | PBMA-b-PDMAEMA | <0.3 | <0.3 | <0.3 | <0.3 |
| P8 | PBMA-b-PDMAEMA | 1 | 2 | 0.24-0.49 | 0.47-0.9 |
| P9 | PBMA-b-PDMAEMA | <0.3 | <0.3 | <0.3 | <0.3 |
| P10 | PBMA-b-PDMAEMA | <0.3 | <0.3 | <0.3 | <0.3 |
| P11 | PBMA-b-DMAEMA | >20 | >20 | 1.25 | 20.00 |
| P12 | PBMA-b-PDMAEMA | <0.3 | 20.00 | <0.3 | 1.25 |
| P13 | PBMA-b-PDMAEMA | >20 | >20 | >20 | >20 |
| P14 | PBMA-b-PDMAEMA | | | | 0.039 |
| P15 | PBMA-b-PDMAEMA | | | | >20 |
| P16 | PBMA-b-PDMAEMA | | | | >20 |
| P17 | PBMA-b-PDMAEMA | | | | >20 |

Antifungal Activity of an Example of Amphiphilic Block Copolymer of the Methacrylic Type in Solution Antifungal tests were carried out on two strains: *Aspergillus niger* and *Candida albicans*. *Aspergillus niger* was seeded on PDA agar dishes and incubated at 35° C. until sporulation (72 h). Once sporulation is reached, 1 ml of 0.85% saline buffer containing Tween 20 is added in order to facilitate dissociation of the mycelium. Once filtered on sterile gauze, the spores are counted and diluted in PD medium so as to reach a concentration close to 5×10E4 CFU/ml. The spores are then added to the compounds diluted in 96-well dishes and incubated for 48 h at 35° C. *Candida albicans* was seeded on an LB agar dish and incubated at 35° C. overnight. On the next day, five colonies are collected from the dish and added to 5 ml of saline buffer. After reading the optical density at 600 nm (1 unit equivalent to $10^7$ CFU/ml), the yeasts are diluted in RPMI+MOPS medium to reach a concentration of $10^3$ CFU/ml. The yeasts are then added to a 96-well plate in the presence of increasing concentrations of compounds and are incubated for 48 h at 35° C. The MIC values are determined for *Aspergillus niger* and *Candida albicans* as the lowest concentration of compound leading to absence of fungal growth evaluated by measuring the absorbance of the wells at 600 nm. The tests show that the compound P14 has an MIC of 40 µM on the fungi.

Anti-Inflammatory Activity of the Amphiphilic Block Copolymers of the Methacrylic Type in Solution The anti-inflammatory activity of the compounds was tested on human monocytes (THP-1 cells) stimulated with lipopolysaccharide (LPS) (extracted from *E. coli* and used at a final concentration of 100 ng/ml). THP-1 cells are seeded on 96-well plates at a rate of $10^4$ cells per well. The cells are then treated with LPS (at 100 ng/ml) in the presence or absence of compounds in increasing concentration. After incubation for 6 h, the culture supernatant is collected before measuring the concentration of TNF-alpha, a cytokine indicative of inflammation and induced by LPS. Polymyxin B, an agent that inhibits the effect of LPS, was used as a positive control. The cellular viability of the THP-1 cells was also measured by the Alamar Blue test. The inhibitory concentrations 50 (IC50) causing 50% inhibition of the production of TNF-alpha or of cellular viability were determined visually (Table 5). The safety factor was determined by dividing the IC50 on production of TNF-alpha by the IC50 on viability.

The results are presented in Table 5.

TABLE 5

| | Block copolymer | IC50 inflammation (µM) | HC50 viability (µM) | Safety Factor |
|---|---|---|---|---|
| P14 | PBMA-b-PDMAEMA | 0.019 | 20 | 1000 |
| P15 | PBMA-b-PDMAEMA | 0.15 | >20 | >100 |
| P16 | PBMA-b-PDMAEMA | 0.039 | >20 | >500 |
| P17 | PBMA-b-PDMAEMA | 0.078 | >20 | >250 |

Method for Preparing the Solid Organic Material by Solvent Evaporation

At the end of bioassays in solution of the copolymers prepared, various solid organic materials were prepared by solvent evaporation based on PS and PMMA containing different amounts of copolymers based on butyl methacrylate (BMA) and N,N-dimethyl-aminoethyl methacrylate (DMAEMA) (quaternized or not), and tested.

The polymer matrices based on PS and PMMA were prepared by the same method of solvent evaporation. For example, in the case of PS, a stock solution of 20 wt % of PS in THF is prepared. 226 mg of copolymer PX (i.e. P1-P17) is dissolved in 5 ml of the solution of PS at 20% in THF to give a copolymer/PS solution at 17 wt %. The same procedure is used for preparing a solution of copolymer at 2 wt %/PS using 22.6 mg of copolymer and 5 ml of the solution of PS 20%/THF. 500 µl of the solution of copolymer at 2 wt %/PS is then diluted with 4.5 ml of the solution of PS20%/THF to give a solution of copolymer/PS at 0.2 wt %. The same method is used for preparing solutions of copolymer/PS at 0.02 wt %. After stirring for 1 hour at room temperature, 150 µl of each solution is poured into each of the 96 wells of a sterile polypropylene microplate (Greiner BioOne). A line of the microplate is earmarked for each of the different concentrations of copolymer and a line is filled with only a solution PS20%/THF as blank test. After 2 days of evaporation of the THF at room temperature, the films of copolymer/PS obtained are then tested for hemolysis and for antimicrobial activity against *E. coli* and *B. subtilis*.

Antimicrobial Activities of a Series of Solid Organic Materials Prepared by Solvent Evaporation The antimicrobial activity of solid organic materials prepared by solvent evaporation containing diblock copolymers P5, P8 and P12 was tested. The antimicrobial activity was evaluated according to an adapted ISO 22196 procedure. The polymer matrix (PS or PMMA) containing the diblock copolymer is put in sterile 96-well polypropylene microplates (Greiner BioOne). Bacterial suspensions are prepared as was done for the MIC tests, except that the bacterial suspension in the logarithmic growth phase (OD600 nm about 0.6) is centrifuged at 6000 rev/min for 10 min at 4° C. The bacterial pellets are washed with 10 ml of phosphate-buffered sterile saline solution (PBS) and centrifuged (6000 rev/min, 10 min, 4° C.). The bacteria are finally diluted in sterile PBS to reach a bacterial density of around $10^{E5}$ bacteria/ml. 10 µl of these suspensions (corresponding to 1000 bacteria) is added to the surface of polymerized copolymers. Negative controls are obtained by adding the 10 µl of bacterial suspension directly onto the surface of the control polymer without adding block copolymer (PMMA or PS). After incubation for 60 minutes at room temperature, the bacteria are collected by adding 90 µl of sterile PBS on the surface and by repeated pipetting up and down. The bacteria are then diluted in series (dilution 1 to 10) in sterile PBS before spreading 10 µl of the bacterial suspension on LB agar plates. After incubation overnight at 37° C., the plates are observed and the colonies are counted. The number of viable bacteria was expressed as a function of the number of colony forming units (CFU) observed. The experiments were carried out in triplicate, independently (n=3). The results of the antimicrobial assays carried out on the solid organic materials are presented in FIGS. 1 to 3.

Hemolytic Characters of a Series of Solid Organic Materials

The hemolytic character of solid organic materials containing diblock copolymers P5, P8 and P12 was tested. 10 µl of suspension of human erythrocytes (8% in PBS) is added to each of the 96 wells of a microplate containing solid organic materials (PS or PMMA with a diblock copolymer). After incubation for 60 minutes at room temperature, 90 µl of PBS is added and the microplate is centrifuged at 800 g for 5 min. 50 µl is then collected carefully from the wells and transferred to a new 96-well microplate and the OD is measured at 405 nm. The hemolysis caused by the copolymers is expressed as percentage hemolysis, Triton-X100 being used as positive control. The results of the hemolytic assays carried out on the solid organic materials are presented in FIGS. 1 to 3.

Figure 2:
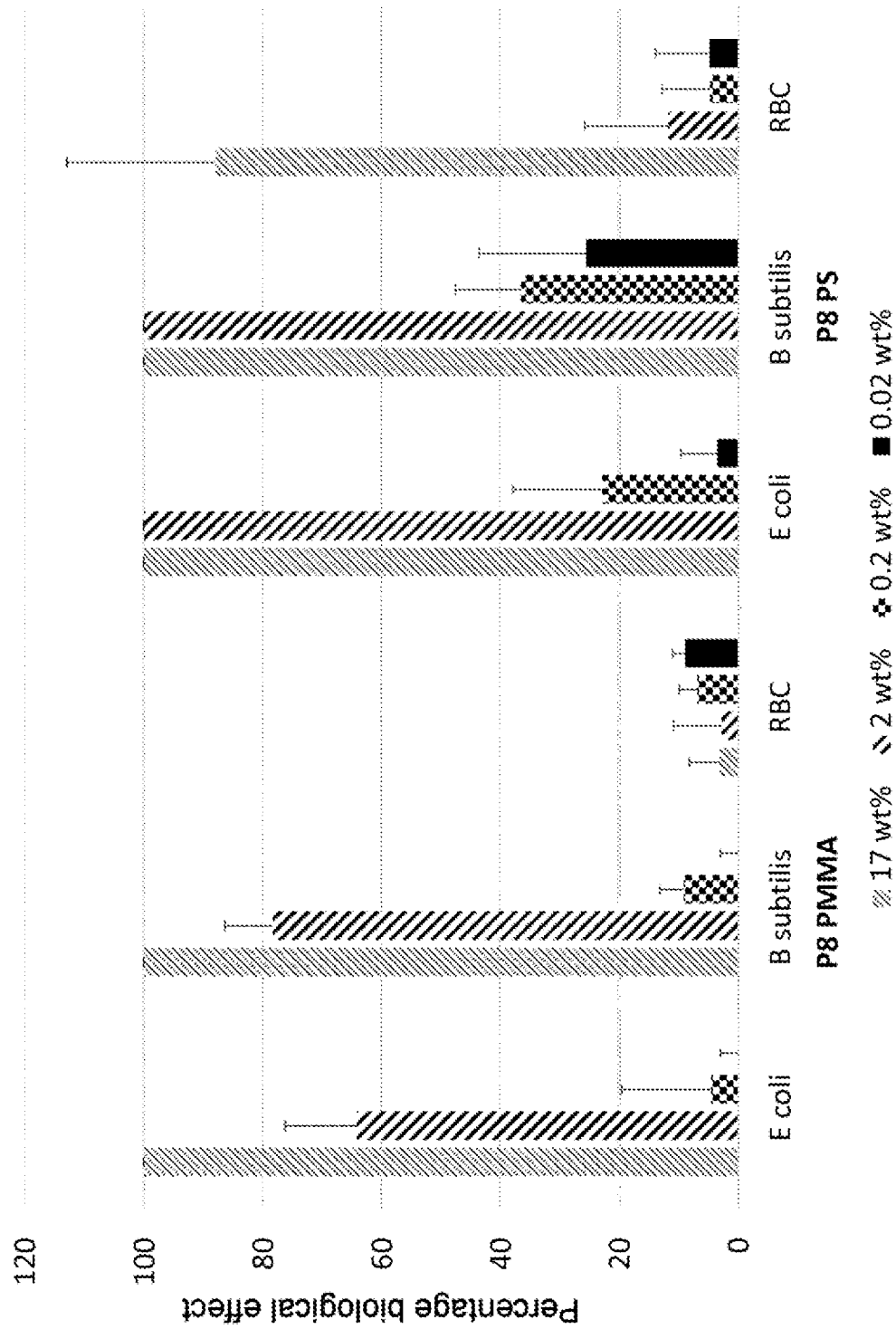
Figure 3:
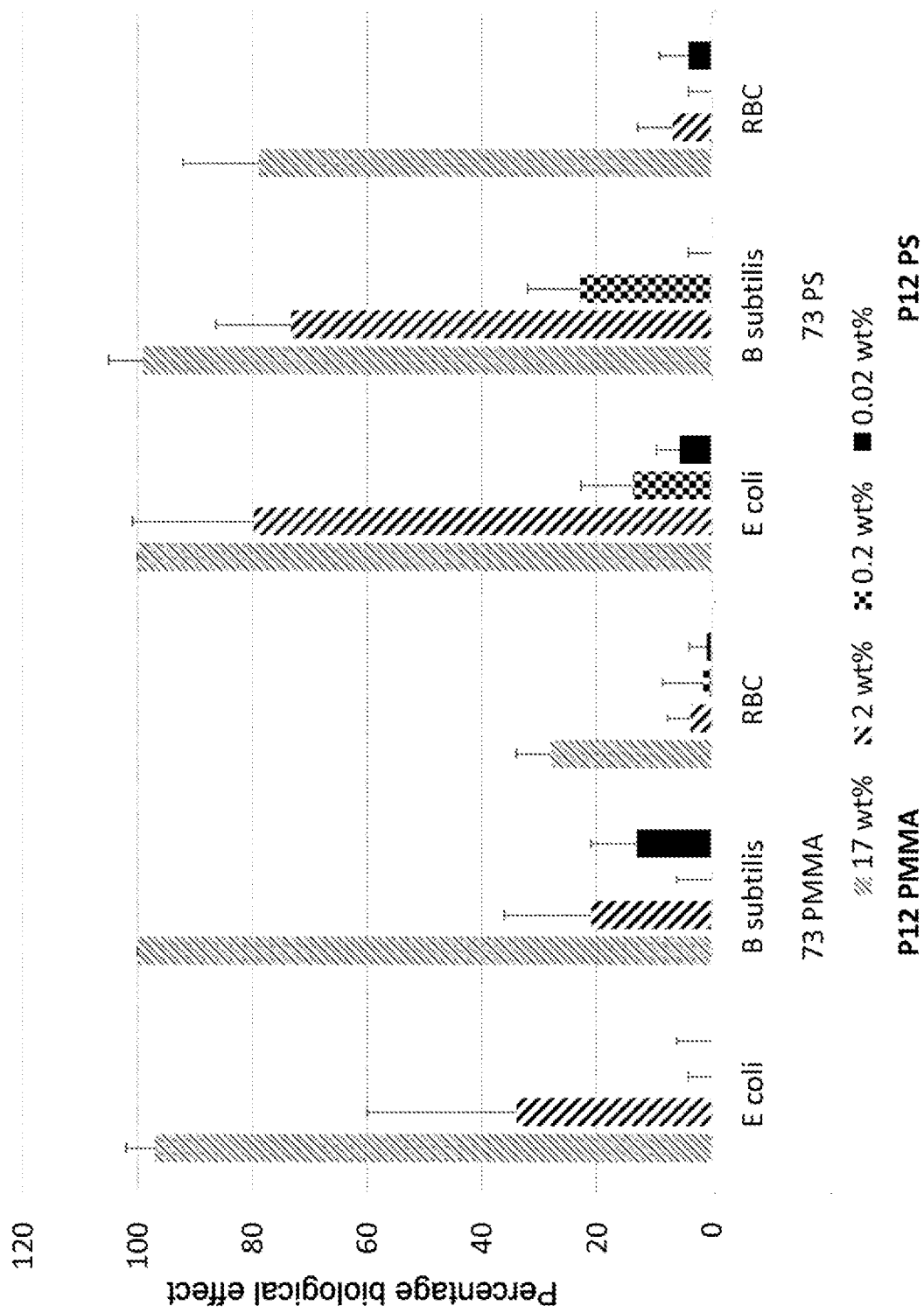

As shown in FIGS. 1 to 3, the tests carried out on *E. coli* and *B. subtilis* show that the solid organic materials prepared are active up to 2 wt %, without any hemolytic character (tests on human red blood cells, RBC).

Although the aforementioned embodiments of the present disclosure are described in detail, it is to be understood that other embodiments may be envisaged. Thus, for example, polymer matrixes other than PMMA or PS may be envisaged for obtaining a solid organic material according to the first aspect; methacrylates other than DMAEMA or DEAEMA may be envisaged for obtaining a solid organic material according to the first aspect; copolymers based on compounds other than MMA, BMA, S and/or ACN may be envisaged for obtaining a solid organic material according to the first aspect.

Method for Preparing the Solid Organic Material by Extrusion

Various solid organic materials based on PS, PMMA and PC (polycarbonate (CALIBRE 201-15 from TRINSEO)) containing different amounts of copolymers based on butyl methacrylate (BMA) and N,N-dimethylamino ethyl methacrylate (DMAEMA) (quaternized or not) were prepared by extrusion.

Dispersion of the copolymer P18 in the solid organic materials was carried out with a Thermo Scientific conical twin-screw mini-extruder (Haake MiniLab II). The temperature and the rotary speed of the screw were adapted to each matrix and are presented in Table 6.

TABLE 6

| Polymer matrix | Supplier | Mw (g/mol) | Extrusion temperature (° C.) | Screw rotary speed (rev/min) |
|---|---|---|---|---|
| PS | Aldrich | 192000 | 180 | 30 |
| PMMA | Aldrich | 120000 | 200 | 100 |
| PC | TRINSEO | — | 220 | 30 |

Before extrusion, the solid organic materials were ground into fine powder and were then mixed with 0.5 wt %/matrix of copolymer P18. 5 g of each mixture was fed manually into the extruder in recirculation mode (1 to 2 min). After 2 min in recirculation mode, the mixture was extruded and recovered in the form of a rod.

Films of solid organic materials were prepared using a Specac Hydraulic press. The mixtures (rods) obtained by extrusion were cut into small pieces and then pressed between two metal disks covered with aluminum film. The pressure was set at 1 tonne and the temperatures are the same as those used in extrusion. The films obtained have an average thickness of 330 µm.

Figure 4:
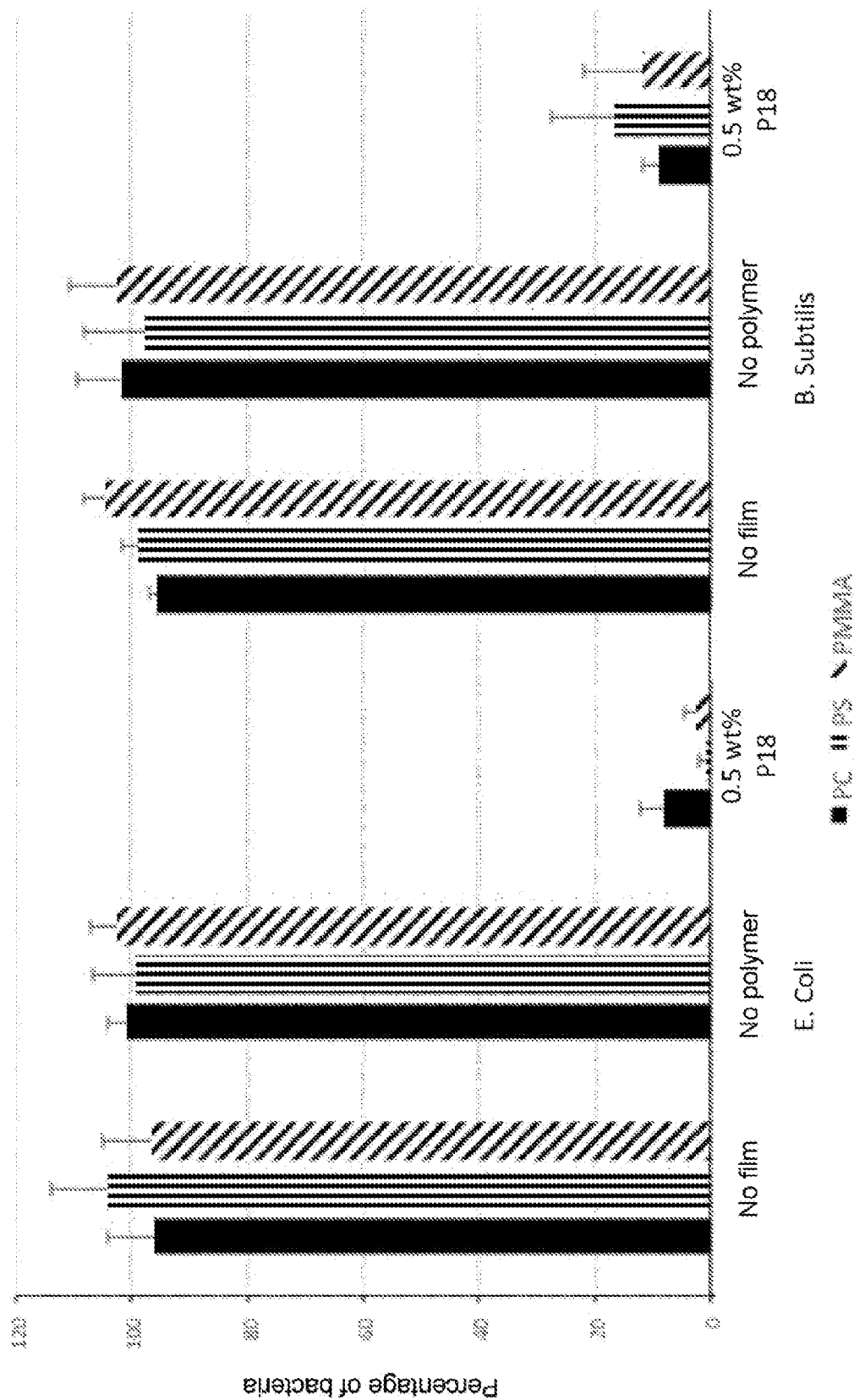

Antimicrobial Activities of a Series of Solid Organic Materials Prepared by Extrusion The antimicrobial activity of solid organic materials prepared by extrusion containing a diblock copolymer P18 was tested. The antimicrobial activity was evaluated according to an adapted ISO 22196 procedure. The polymer matrix (PS, PMMA, polycarbonate) containing the diblock copolymer is introduced into sterile 96-well polypropylene microplates (Greiner BioOne). Bacterial suspensions are prepared as for the MIC tests, except that the bacterial suspension in the logarithmic growth phase (OD600 nm about 0.6) is centrifuged at 6000 rev/min for 10 min at 4° C. The bacterial pellets are washed with 10 ml of sterile phosphate-buffered saline solution (PBS) and centrifuged (6000 rev/min, 10 min, 4° C.). The bacteria are finally diluted in sterile PBS to reach a bacterial density of around $10^{E5}$ bacteria/ml. 10 µl of these suspensions (corresponding to 1000 bacteria) is added onto the surface of polymerized copolymers. Negative controls are obtained by adding the bacterial suspension of 10 µl directly either in a control well not containing film ("no film" sample, FIG. 4), or on a film of the extruded solid organic material not containing the copolymer P18 ("no polymer" sample, FIG. 4). After incubation for 60 minutes at room temperature, the bacteria are collected by adding 90 µl of sterile PBS on the surface and by repeated pipetting up and down. The bacteria are then series-diluted (dilution 1 to 10) in sterile PBS before spreading 10 µl of the bacterial suspension on LB agar plates. After incubation overnight at 37° C., the plates are observed and the colonies are counted. The number of viable bacteria was expressed as a function of the number of colony forming units (CFU) observed. The experiments were carried out in triplicate independently (n=3). The results of the antimicrobial assays carried out on the solid organic materials prepared by extrusion are presented in FIG. 4.

The invention claimed is:

1. A medical device comprising a solid organic material, wherein the solid organic material comprises at least one amphiphilic block copolymer of the methacrylic type, said amphiphilic block copolymer being dispersed in a polymer matrix and having a number-average molar mass (Mn) greater than or equal to 20 000 g/mol, wherein said amphiphilic block copolymer comprises at least one hydrophilic methacrylic block consisting of a first hydrophilic repeating unit being N,N-(dialkylamino)alkyl methacrylate and a second hydrophilic repeating unit being a quaternary ammonium ion of the latter.

2. The medical device as claimed in claim 1, selected from the group consisting of a catheter.

* * * * *